(12) United States Patent
Sales et al.

(10) Patent No.: US 10,448,867 B2
(45) Date of Patent: Oct. 22, 2019

(54) WEARABLE GAIT MONITORING APPARATUS, SYSTEMS, AND RELATED METHODS

(71) Applicant: Vision Service Plan, Rancho Cordova, CA (US)

(72) Inventors: Jay William Sales, Citrus Heights, CA (US); Richard Chester Klosinski, Jr., Sacramento, CA (US); Matthew Allen Workman, Sacramento, CA (US); Meghan Kathleen Murphy, Davis, CA (US); Matthew David Steen, Sacramento, CA (US)

(73) Assignee: Vision Service Plan, Rancho Cordova, CA (US)

( * ) Notice: Subject to any disclaimer, the term of this patent is extended or adjusted under 35 U.S.C. 154(b) by 1095 days.

(21) Appl. No.: 14/550,406

(22) Filed: Nov. 21, 2014

(65) Prior Publication Data

US 2016/0066820 A1    Mar. 10, 2016

Related U.S. Application Data (60) Provisional application No. 62/046,406, filed on Sep. 5, 2014.

(51) Int. Cl.
*A61B 5/11*     (2006.01)
*A61B 5/00*     (2006.01)
(Continued)

(52) U.S. Cl.
CPC .............. *A61B 5/112* (2013.01); *A61B 3/112* (2013.01); *A61B 5/0002* (2013.01);
(Continued)

(58) Field of Classification Search
CPC ...................................................... A61B 5/112
See application file for complete search history.

(56) References Cited

U.S. PATENT DOCUMENTS 3,505,879 A    4/1970   Vanderberg
3,548,663 A    12/1970  Radin
(Continued)

FOREIGN PATENT DOCUMENTS

EP    2778612     12/2017
GB    2396421     6/2004
(Continued)

OTHER PUBLICATIONS

Michael Franco, Tzoa wearable turns you into a walking air-quality sensor, Dec. 9, 2014, CNET, https://www.cnet.com/news/tzoa-wearable-turns-you-into-a-walking-air-quality-sensor/.
(Continued)

*Primary Examiner* — Rene T Towa
(74) *Attorney, Agent, or Firm* — Brient IP Law, LLC (57) ABSTRACT

A system, according to various embodiments, includes eyewear (or any other suitable wearable device) that includes one or more sensors (e.g., one or more accelerometers, magnetometers, position sensors, gyroscopes, and/or other suitable sensors) that may be used to monitor the gait of an individual (e.g., by monitoring the movement of the user's head, or other portions of the user's body, as the user ambulates). The system may further include one or more suitable computing devices for analyzing the individual's gait. This information may then be used, for example, to: (1) identify one or more medical conditions associated with the individual; (2) assess the fit of a prosthetic device worn by the individual, and/or (3) assess an individual's recovery from a particular injury or medical procedure.

13 Claims, 3 Drawing Sheets

(51) Int. Cl.

| | | |
|---|---|---|
| A61B 3/11 | (2006.01) | |
| A61B 5/0402 | (2006.01) | |
| A61B 5/0476 | (2006.01) | |
| A61B 5/103 | (2006.01) | |
| A61B 5/1171 | (2016.01) | |
| A61B 5/16 | (2006.01) | |
| A61B 7/04 | (2006.01) | |
| G09B 5/00 | (2006.01) | |
| A61B 5/1455 | (2006.01) | |
| G06K 9/00 | (2006.01) | |
| G06K 9/62 | (2006.01) | |
| G08B 21/04 | (2006.01) | |
| A63B 24/00 | (2006.01) | |
| G09B 5/06 | (2006.01) | |
| G09B 19/00 | (2006.01) | |
| G06F 19/00 | (2018.01) | |
| G06F 21/35 | (2013.01) | |
| G07C 9/00 | (2006.01) | |
| G08B 21/02 | (2006.01) | |
| H04L 29/06 | (2006.01) | |
| G16H 40/63 | (2018.01) | |
| G16H 50/20 | (2018.01) | |
| A61B 5/117 | (2016.01) | |
| G16H 20/40 | (2018.01) | |
| A61F 2/76 | (2006.01) | |
| A61B 5/0205 | (2006.01) | |
| A61B 5/024 | (2006.01) | |
| A61B 5/053 | (2006.01) | |
| A61B 5/08 | (2006.01) | |
| G02C 11/00 | (2006.01) | |

(52) U.S. Cl.
CPC .......... *A61B 5/0022* (2013.01); *A61B 5/0077* (2013.01); *A61B 5/0402* (2013.01); *A61B 5/0476* (2013.01); *A61B 5/1032* (2013.01); *A61B 5/1103* (2013.01); *A61B 5/117* (2013.01); *A61B 5/1114* (2013.01); *A61B 5/1116* (2013.01); *A61B 5/1128* (2013.01); *A61B 5/1176* (2013.01); *A61B 5/14552* (2013.01); *A61B 5/165* (2013.01); *A61B 5/4076* (2013.01); *A61B 5/4266* (2013.01); *A61B 5/443* (2013.01); *A61B 5/486* (2013.01); *A61B 5/4884* (2013.01); *A61B 5/6803* (2013.01); *A61B 5/7246* (2013.01); *A61B 5/7278* (2013.01); *A61B 7/04* (2013.01); *A63B 24/0062* (2013.01); *G06F 19/00* (2013.01); *G06F 19/3481* (2013.01); *G06F 21/35* (2013.01); *G06K 9/00348* (2013.01); *G06K 9/00597* (2013.01); *G06K 9/00604* (2013.01); *G06K 9/00617* (2013.01); *G06K 9/00664* (2013.01); *G06K 9/6201* (2013.01); *G07C 9/00158* (2013.01); *G08B 21/02* (2013.01); *G08B 21/0423* (2013.01); *G08B 21/0461* (2013.01); *G08B 21/0476* (2013.01); *G09B 5/00* (2013.01); *G09B 5/06* (2013.01); *G09B 19/0092* (2013.01); *G16H 20/40* (2018.01); *G16H 40/63* (2018.01); *G16H 50/20* (2018.01); *H04L 63/0861* (2013.01); *A61B 5/024* (2013.01); *A61B 5/0205* (2013.01); *A61B 5/0531* (2013.01); *A61B 5/0816* (2013.01); *A61B 5/1118* (2013.01); *A61B 5/7282* (2013.01); *A61B 2560/0475* (2013.01); *A61B 2562/0219* (2013.01); *A61B 2562/0223* (2013.01); *A61B 2562/0257* (2013.01); *A61B 2576/00* (2013.01); *A61F 2/76* (2013.01); *A61F 2002/7695* (2013.01); *G02C 11/10* (2013.01)

(56) References Cited

U.S. PATENT DOCUMENTS

| | | |
|---|---|---|
| 3,972,038 A | 7/1976 | Nasa |
| 4,100,401 A | 7/1978 | Tutt et al. |
| 4,186,609 A | 2/1980 | Baermann |
| 4,195,642 A | 4/1980 | Price et al. |
| 4,281,663 A | 8/1981 | Pringle |
| 4,407,295 A | 10/1983 | Steuer et al. |
| 4,434,801 A | 3/1984 | Jiminez et al. |
| 4,855,942 A | 8/1989 | Bianco |
| 4,878,749 A | 11/1989 | McGee |
| 4,919,530 A | 4/1990 | Hyman |
| 5,422,816 A | 6/1995 | Sprague et al. |
| 5,452,480 A | 9/1995 | Ryden |
| 5,497,143 A | 3/1996 | Matsuo et al. |
| 5,585,871 A | 12/1996 | Linden |
| 5,670,872 A | 9/1997 | Van De Walle et al. |
| 5,746,501 A | 5/1998 | Chien et al. |
| 5,891,042 A | 4/1999 | Sham et al. |
| 5,931,764 A | 8/1999 | Freeman et al. |
| 5,966,680 A | 10/1999 | Butnaru |
| 5,976,083 A | 11/1999 | Richardson et al. |
| 6,013,007 A | 1/2000 | Root et al. |
| 6,183,425 B1 | 2/2001 | Whalen et al. |
| 6,218,958 B1 | 4/2001 | Eichstaedt et al. |
| 6,241,684 B1 | 6/2001 | Amano et al. |
| 6,325,507 B1 | 12/2001 | Jannard et al. |
| 6,381,482 B1 | 4/2002 | Jayaraman et al. |
| 6,431,705 B1 | 8/2002 | Linden et al. |
| 6,439,067 B1 | 8/2002 | Goldman et al. |
| 6,513,532 B2 | 2/2003 | Mault et al. |
| 6,532,298 B1 | 3/2003 | Cambier et al. |
| 6,736,759 B1 | 5/2004 | Stubbs et al. |
| 6,769,767 B2 | 8/2004 | Swab et al. |
| 6,783,501 B2 | 8/2004 | Takahashi et al. |
| 6,790,178 B1 | 9/2004 | Mault et al. |
| 6,812,845 B2 | 11/2004 | Yuzuki et al. |
| 7,181,345 B2 | 2/2007 | Rosenfeld et al. |
| 7,187,960 B2 | 3/2007 | Abreu |
| 7,192,136 B2 | 3/2007 | Howell et al. |
| 7,255,437 B2 | 8/2007 | Howell et al. |
| 7,376,238 B1 | 5/2008 | Rivas et al. |
| 7,380,936 B2 | 6/2008 | Howell et al. |
| 7,400,257 B2 | 7/2008 | Rivas |
| 7,401,918 B2 | 7/2008 | Howell et al. |
| 7,438,410 B1 | 10/2008 | Howell et al. |
| 7,454,002 B1 | 11/2008 | Gardner et al. |
| 7,457,434 B2 | 11/2008 | Azar |
| 7,481,531 B2 | 1/2009 | Howell et al. |
| 7,488,294 B2 | 2/2009 | Torch |
| 7,500,746 B1 | 3/2009 | Howell et al. |
| 7,500,747 B2 | 3/2009 | Howell et al. |
| 7,515,054 B2 | 4/2009 | Torch |
| 7,543,934 B2 | 6/2009 | Howell et al. |
| 7,581,833 B2 | 9/2009 | Howell et al. |
| 7,621,634 B2 | 11/2009 | Howell et al. |
| 7,630,524 B2 | 12/2009 | Lauper et al. |
| 7,634,379 B2 | 12/2009 | Noble |
| 7,640,135 B2 | 12/2009 | Vock et al. |
| 7,648,463 B1 | 1/2010 | Elhag et al. |
| 7,677,723 B2 | 3/2010 | Howell et al. |
| 7,771,046 B2 | 8/2010 | Howell et al. |
| 7,792,552 B2 | 9/2010 | Thomas et al. |
| 7,793,361 B2 | 9/2010 | Ishihara et al. |
| 7,857,772 B2 | 9/2010 | Bouvier et al. |
| 7,806,525 B2 | 10/2010 | Howell et al. |
| 7,922,321 B2 | 4/2011 | Howell et al. |
| 7,987,070 B2 | 7/2011 | Kahn et al. |
| 8,011,242 B2 | 9/2011 | O'Neill et al. |
| 8,081,082 B2 | 12/2011 | Malik et al. |
| 8,109,629 B2 | 2/2012 | Howell et al. |
| 8,188,868 B2 | 5/2012 | Case |

(56) References Cited

U.S. PATENT DOCUMENTS

| | | | |
|---|---|---|---|
| 8,202,148 B2 | 6/2012 | Young |
| 8,294,581 B2 | 10/2012 | Kamen |
| 8,303,311 B2 | 11/2012 | Forest |
| 8,337,013 B2 | 12/2012 | Howell et al. |
| 8,384,617 B2 | 2/2013 | Braun et al. |
| 8,430,507 B2 | 4/2013 | Howell et al. |
| 8,448,846 B2 | 5/2013 | Needham et al. |
| 8,449,471 B2 | 5/2013 | Tran |
| 8,465,151 B2 | 6/2013 | Howell et al. |
| 8,494,507 B1 | 7/2013 | Tedesco et al. |
| 8,500,271 B2 | 8/2013 | Howell et al. |
| 8,510,166 B2 | 8/2013 | Neven |
| 8,531,355 B2 | 9/2013 | Maltz |
| 8,540,583 B2 | 9/2013 | Leech |
| 8,568,313 B2 | 10/2013 | Sadhu |
| 8,594,971 B2 | 11/2013 | Keal et al. |
| 8,620,600 B2 | 12/2013 | Vock et al. |
| 8,630,633 B1 | 1/2014 | Tedesco et al. |
| 8,634,701 B2 | 1/2014 | Kang et al. |
| 8,647,270 B2 | 2/2014 | Leboeuf et al. |
| 8,690,750 B2 | 4/2014 | Krueger |
| 8,696,113 B2 | 4/2014 | Lewis |
| 8,733,928 B1 | 5/2014 | Lewis |
| 8,750,971 B2 | 6/2014 | Tran |
| 8,764,651 B2 | 7/2014 | Tran |
| 8,849,610 B2 | 9/2014 | Molettiere et al. |
| 8,892,401 B2 | 11/2014 | Yuen et al. |
| 8,905,542 B2 | 12/2014 | Howell et al. |
| 8,911,087 B2 | 12/2014 | Publicover et al. |
| 8,920,332 B2 | 12/2014 | Hong et al. |
| 8,931,896 B2 | 1/2015 | Blum et al. |
| 8,941,560 B2 | 1/2015 | Wong et al. |
| 8,944,590 B2 | 2/2015 | Blum et al. |
| 8,961,415 B2 | 2/2015 | Leboeuf et al. |
| 8,964,298 B2 | 2/2015 | Haddick et al. |
| 8,965,730 B2 | 2/2015 | Yuen |
| 8,979,295 B2 | 3/2015 | Waters |
| 9,001,427 B2 | 4/2015 | Jacobs et al. |
| 9,005,129 B2 | 4/2015 | Venkatraman et al. |
| 9,007,220 B2 | 4/2015 | Johns et al. |
| 9,028,405 B2 | 5/2015 | Tran |
| 9,033,493 B2 | 5/2015 | Howell et al. |
| 9,035,970 B2 | 5/2015 | Lamb et al. |
| 9,064,342 B2 | 6/2015 | Yuen et al. |
| 9,112,701 B2 | 8/2015 | Sano et al. |
| 9,113,794 B2 | 8/2015 | Hong et al. |
| 9,113,795 B2 | 8/2015 | Hong et al. |
| 9,141,194 B1 | 9/2015 | Keyes et al. |
| 9,144,405 B2 | 9/2015 | Kim et al. |
| 9,153,074 B2 | 10/2015 | Zhou et al. |
| 9,215,290 B2 | 12/2015 | Yuen et al. |
| 9,229,227 B2 | 1/2016 | Border et al. |
| 9,235,064 B2 | 1/2016 | Lewis |
| 9,239,473 B2 | 1/2016 | Lewis |
| 9,241,635 B2 | 1/2016 | Yuen et al. |
| 9,244,293 B2 | 1/2016 | Lewis |
| 9,247,212 B2 | 1/2016 | Bose et al. |
| 9,254,100 B2 | 2/2016 | Beck et al. |
| 9,256,711 B2 | 2/2016 | Horseman |
| 9,304,331 B2 | 4/2016 | Carrara |
| 9,341,526 B2 | 5/2016 | Bass et al. |
| 9,342,610 B2 | 5/2016 | Liu et al. |
| 9,480,877 B2 | 11/2016 | Chiang et al. |
| 9,520,638 B2 | 12/2016 | Baringer et al. |
| 9,529,197 B2 | 12/2016 | Olsson et al. |
| 9,566,033 B2 | 2/2017 | Bogdanovich et al. |
| 9,579,060 B1 | 2/2017 | Lisy et al. |
| 9,610,476 B1 | 4/2017 | Tran et al. |
| 9,726,904 B1 | 8/2017 | Lin |
| 9,763,592 B2 | 9/2017 | Le et al. |
| 9,896,154 B2 | 2/2018 | Modolo |
| 9,977,259 B2 | 5/2018 | Archambeau et al. |
| 10,188,323 B2 | 1/2019 | Sales et al. |
| 10,310,296 B2 | 6/2019 | Howell et al. |
| 10,330,956 B2 | 6/2019 | Howell et al. |
| 2001/0031031 A1 | 10/2001 | Ogawa et al. |
| 2002/0151810 A1 | 10/2002 | Wong et al. |
| 2003/0195398 A1 | 10/2003 | Suzuki et al. |
| 2004/0039517 A1 | 2/2004 | Biesinger et al. |
| 2005/0033200 A1 | 2/2005 | Soehren et al. |
| 2005/0036103 A1 | 2/2005 | Bloch |
| 2005/0054942 A1 | 3/2005 | Melker et al. |
| 2006/0115130 A1 | 6/2006 | Kozlay |
| 2007/0052672 A1 | 3/2007 | Ritter et al. |
| 2007/0112287 A1 | 5/2007 | Fancourt et al. |
| 2007/0273611 A1 | 11/2007 | Torch |
| 2008/0045804 A1* | 2/2008 | Williams ............... A61B 5/112 600/300 |
| 2008/0137916 A1 | 6/2008 | Lauper et al. |
| 2008/0146892 A1* | 6/2008 | LeBoeuf ............. A61B 5/0205 600/300 |
| 2009/0030350 A1* | 1/2009 | Yang ................... A61B 5/1038 600/595 |
| 2009/0195747 A1 | 8/2009 | Insua |
| 2009/0227853 A1 | 9/2009 | Wijesiriwardana |
| 2009/0267805 A1 | 10/2009 | Jin et al. |
| 2010/0042430 A1 | 2/2010 | Bartfeld |
| 2010/0045928 A1 | 2/2010 | Levy |
| 2010/0110368 A1 | 5/2010 | Chaum |
| 2010/0136508 A1 | 6/2010 | Zekhtser |
| 2010/0271587 A1 | 10/2010 | Pavlopoulos |
| 2010/0280336 A1 | 11/2010 | Giftakis et al. |
| 2010/0308999 A1 | 12/2010 | Chornenky |
| 2010/0332571 A1 | 12/2010 | Healey et al. |
| 2011/0169932 A1 | 7/2011 | Mula et al. |
| 2011/0221656 A1 | 9/2011 | Haddick et al. |
| 2011/0224505 A1 | 9/2011 | Sadhu |
| 2012/0021806 A1 | 1/2012 | Maltz |
| 2012/0029367 A1 | 2/2012 | Hobeika |
| 2012/0127423 A1 | 5/2012 | Blum et al. |
| 2012/0133885 A1 | 5/2012 | Howell et al. |
| 2012/0135384 A1 | 5/2012 | Nakao |
| 2012/0142443 A1 | 6/2012 | Savarese et al. |
| 2012/0169990 A1 | 7/2012 | Burnstein |
| 2012/0191016 A1* | 7/2012 | Jastram ............... A61B 5/0002 600/595 |
| 2012/0203310 A1 | 8/2012 | Pugh et al. |
| 2012/0206485 A1 | 8/2012 | Osterhout et al. |
| 2012/0209149 A1* | 8/2012 | Yoneyama ............. A61B 5/112 600/595 |
| 2012/0310442 A1 | 12/2012 | Doutaz et al. |
| 2013/0009907 A1 | 1/2013 | Rosenberg et al. |
| 2013/0024022 A1 | 1/2013 | Bowers |
| 2013/0024211 A1 | 1/2013 | Monteforte et al. |
| 2013/0041590 A1 | 2/2013 | Burich et al. |
| 2013/0050258 A1 | 2/2013 | Liu et al. |
| 2013/0096397 A1 | 4/2013 | Kiso et al. |
| 2013/0138413 A1 | 5/2013 | Finch et al. |
| 2013/0157232 A1 | 6/2013 | Ehrenkranz |
| 2013/0242262 A1 | 9/2013 | Lewis |
| 2013/0274587 A1 | 10/2013 | Coza et al. |
| 2013/0274904 A1 | 10/2013 | Coza et al. |
| 2013/0307670 A1 | 11/2013 | Ramaci |
| 2013/0329183 A1 | 12/2013 | Blum et al. |
| 2013/0345168 A1 | 12/2013 | Kim et al. |
| 2014/0028456 A1 | 1/2014 | Sadhu |
| 2014/0031703 A1 | 1/2014 | Rayner et al. |
| 2014/0063242 A1 | 3/2014 | Hanina et al. |
| 2014/0073081 A1 | 3/2014 | Wang |
| 2014/0078049 A1 | 3/2014 | Parshionikar |
| 2014/0085190 A1 | 3/2014 | Erinjippurath et al. |
| 2014/0135593 A1 | 5/2014 | Jayalth et al. |
| 2014/0142459 A1 | 5/2014 | Jayalth et al. |
| 2014/0159862 A1 | 6/2014 | Yang et al. |
| 2014/0204334 A1 | 7/2014 | Stoll |
| 2014/0207264 A1 | 7/2014 | Quy |
| 2014/0218281 A1 | 8/2014 | Amayeh et al. |
| 2014/0228649 A1 | 8/2014 | Rayner et al. |
| 2014/0229220 A1 | 8/2014 | Yuen et al. |
| 2014/0240122 A1* | 8/2014 | Roberts ............... A61B 5/0022 340/539.11 |
| 2014/0247145 A1 | 9/2014 | Proud |
| 2014/0266988 A1 | 9/2014 | Fisher et al. |

(56) References Cited

U.S. PATENT DOCUMENTS

| | | | |
|---|---|---|---|
| 2014/0276096 A1* | 9/2014 | Bonutti | A61B 5/7275 600/476 |
| 2014/0340221 A1 | 11/2014 | Yuen et al. | |
| 2014/0346158 A1 | 11/2014 | Matthews | |
| 2014/0375452 A1 | 12/2014 | Yuen et al. | |
| 2014/0375470 A1 | 12/2014 | Malveaux | |
| 2014/0378872 A1 | 12/2014 | Hong et al. | |
| 2015/0057512 A1 | 2/2015 | Kapoor | |
| 2015/0085245 A1 | 3/2015 | Howell et al. | |
| 2015/0088464 A1 | 3/2015 | Yuen et al. | |
| 2015/0173631 A1 | 6/2015 | Richards et al. | |
| 2015/0179050 A1 | 6/2015 | Katingari et al. | |
| 2015/0185506 A1 | 7/2015 | Lewis | |
| 2015/0212329 A1 | 7/2015 | Sugihara et al. | |
| 2015/0223805 A1 | 8/2015 | Whitman et al. | |
| 2015/0244910 A1 | 8/2015 | Marston et al. | |
| 2015/0281879 A1 | 10/2015 | Saadi | |
| 2015/0287338 A1 | 10/2015 | Wells et al. | |
| 2015/0332149 A1 | 11/2015 | Kolb et al. | |
| 2015/0342482 A1 | 12/2015 | Carrara | |
| 2015/0366518 A1 | 12/2015 | Sampson | |
| 2016/0007849 A1 | 1/2016 | Krueger | |
| 2016/0034042 A1 | 2/2016 | Joo | |
| 2016/0041404 A1 | 2/2016 | Palermo et al. | |
| 2016/0041613 A1 | 2/2016 | Klanner et al. | |
| 2016/0117937 A1 | 4/2016 | Penders et al. | |
| 2016/0314468 A1 | 10/2016 | Smith et al. | |
| 2017/0323584 A1 | 11/2017 | Daniel et al. | |

FOREIGN PATENT DOCUMENTS

| | | |
|---|---|---|
| WO | 2005015163 | 2/2005 |
| WO | 2005094667 | 10/2005 |
| WO | 2007088374 | 8/2007 |
| WO | 2008073806 | 6/2008 |
| WO | 2010006370 | 1/2010 |
| WO | 2010062479 | 6/2010 |
| WO | 2010062481 | 6/2010 |
| WO | 2011086466 | 7/2011 |
| WO | 2012041485 | 4/2012 |
| WO | 2013188343 | 12/2013 |
| WO | 2014021602 | 2/2014 |
| WO | 2014108481 | 7/2014 |
| WO | 2014144918 | 9/2014 |
| WO | 2014144940 | 9/2014 |
| WO | 2014170280 | 10/2014 |
| WO | 2014188244 | 11/2014 |
| WO | 2015015025 | 2/2015 |
| WO | 2015081299 | 6/2015 |
| WO | 2015095924 | 7/2015 |
| WO | 2015127143 | 8/2015 |
| WO | 2015127441 | 8/2015 |
| WO | 2016017997 | 2/2016 |
| WO | 2016029803 | 3/2016 |

OTHER PUBLICATIONS

Notice of Allowance, dated Feb. 28, 2017, from corresponding U.S. Appl. No. 14/588,122.
Office Action, dated Feb. 10, 2017, from corresponding U.S. Appl. No. 14/846,401.
Office Action, dated Mar. 3, 2017, from corresponding U.S. Appl. No. 14/610,628.
International Preliminary Report on Patentability, dated Mar. 16, 2017, from corresponding International Application No. PCT/US2015/048662.
Ted Burnham, Wearable Air Quality Sensor: Tzoa, Jan. 5, 2015, Postscapes, http://www.postscapes.com/wearable-air-quality-sensor-tzoa/.
Final Office Action, dated Mar. 29, 2017, from corresponding U.S. Appl. No. 14/562,454.
International Preliminary Report on Patentability, dated Mar. 16, 2017, from corresponding International Application No. PCT/US2015/048612.
International Preliminary Report on Patentability, dated Mar. 16, 2017, from corresponding International Application No. PCT/US2015/048656.
Final Office Action, dated Dec. 15, 2016, from corresponding U.S. Appl. No. 14/506,249.
Final Office Action, dated Sep. 26, 2016, from corresponding U.S. Appl. No. 14/610,628.
International Search Report, dated Jan. 21, 2016, from corresponding International Application No. PCT/US2015/048612.
International Search Report, dated Jan. 21, 2016, from corresponding International Application No. PCT/US2015/048656.
International Search Report, dated Jun. 2, 2016, from corresponding International Application No. PCT/US2016/015705.
Invitation to Pay Additional Search Fees, dated Apr. 1, 2016, from corresponding International Application Serial No. PCT/US2016/015705.
Maria S. Redin, "Marathon Man", Article Jun. 15, 1998, MIT Media Laboratory.
Office Action, dated Aug. 19, 2016, from corresponding U.S. Appl. No. 14/578,039.
Office Action, dated Jul. 1, 2016, from corresponding U.S. Appl. No. 14/562,454.
Office Action, dated Jul. 22, 2016, from corresponding U.S. Appl. No. 14/506,249.
Office Action, dated Mar. 8, 2016, from corresponding U.S. Appl. No. 14/610,628.
Office Action, dated Sep. 2, 2016, from corresponding U.S. Appl. No. 14/588,122.
Restriction Requirement, dated Nov. 10, 2016, from corresponding U.S. Appl. No. 14/846,401.
Richard M. Satava, et al., "The Physiologic Cipher at Altitude: Telemedicine and Real-Time Monitoring of Climbers on Mount Everest", Telemedicine Journal and e-Health, vol. 6, No. 3, 2000, Mary Ann Liebert, Inc.
Written Opinion of the International Searching Authority, dated Jan. 21, 2016, from corresponding International Application No. PCT/US2015/048612.
Written Opinion of the International Searching Authority, dated Jan. 21, 2016, from corresponding International Application No. PCT/US2015/048656.
Written Opinion of the International Searching Authority, dated Jun. 2, 2016, from corresponding International Application No. PCT/US2016/015705.
Office Action, dated Dec. 29, 2016, from corresponding U.S. Appl. No. 14/610,589.
Phend, Crystal, "Calorie Intake Rises as Sleep Time Drops," Medpage Today, Medpage Today, LLC, Mar. 15, 2012, Web Dec. 19, 2016, http://www.medpagetoday.com/cardiology/prevention/31663.
Final Office Action, dated Jun. 30, 2017, from corresponding U.S. Appl. No. 14/610,589.
Shankland, Stephen, "Google's electronic eyewear get 'OK Glass' voice commands", Feb. 20, 2013, Cnet.com, https://www.cnet.com/news/googles-electronic-eyewear-gets-ok-glass-voice-commands/.
Office Action, dated Jun. 29, 2017, from corresponding U.S. Appl. No. 15/489,147.
Final Office Action, dated Jul. 10, 2017, from corresponding U.S. Appl. No. 14/846,401.
Final Office Action, dated May 23, 2017, from corresponding U.S. Appl. No. 14/578,039.
Notice of Allowance, dated Jun. 21, 2017, from corresponding U.S. Appl. No. 14/562,454.
Office Action, dated Jun. 27, 2017, from corresponding U.S. Appl. No. 15/060,333.
Tolentino, Mellisa, Udderly Clever Wearable Tech Solutions, http://siliconangle.com/blog/2014/03/25/udderly-clever-wearable-tech-solutions/, Mar. 25, 2014.
Torres, Juan Carlos, ODG R-7 Smart Glasses Carries Its Own Android Inside, http://androidcommunity.com/pdg-r-7-smart-glasses-carries-its-own-android-inside-20140919/, Sep. 19, 2014.

(56) References Cited

OTHER PUBLICATIONS

Invitation to Pay Additional Search Fees, dated Nov. 4, 2015, from corresponding International Application Serial No. PCT/US2015/048612.
Invitation to Pay Additional Search Fees, dated Nov. 4, 2015, from corresponding International Application Serial No. PCT/US2015/048656.
International Search Report, dated Dec. 18, 2015, from corresponding International Application No. PCT/US2015/048662.
Written Opinion of the International Searching Authority, dated Dec. 18, 2015, from corresponding International Application No. PCT/US2015/048662.
Office Action, dated Jan. 11, 2018, from corresponding U.S. Appl. No. 15/074,679.
Office Action, dated Mar. 2, 2018, from corresponding U.S. Appl. No. 15/060,333.
Office Action, dated Mar. 9, 2018, from corresponding U.S. Appl. No. 14/610,439.
Final Office Action, dated Mar. 30, 2018, from corresponding U.S. Appl. No. 14/846,401.
Office Action, dated May 23, 2018, from corresponding U.S. Appl. No. 14/578,039.
Office Action, dated Sep. 29, 2017, from corresponding U.S. Appl. No. 14/506,249.
Office Action, dated Sep. 26, 2017, from corresponding U.S. Appl. No. 14/846,401.
Restriction Requirement, dated Oct. 4, 2017, from corresponding U.S. Appl. No. 14/610,439.
Notice of Allowance, dated Oct. 20, 2017, from corresponding U.S. Appl. No. 15/489,147.
Final Office Action, dated Nov. 16, 2017, from corresponding U.S. Appl. No. 14/610,628.
Notice of Allowance, dated Dec. 13, 2017, from corresponding U.S. Appl. No. 14/610,501.
Final Office Action, dated Sep. 25, 2018, from corresponding U.S. Appl. No. 14/610,439.
Notice of Allowance, dated Sep. 13, 2018, from corresponding U.S. Appl. No. 15/594,898.
Office Action, dated Sep. 11, 2018, from corresponding U.S. Appl. No. 15/060,333.
Office Action, dated Oct. 4, 2018, from corresponding U.S. Appl. No. 15/791,196.
Office Action, dated Jun. 8, 2018, from corresponding U.S. Appl. No. 14/610,501.
Final Office Action, dated Jun. 14, 2018, from corresponding U.S. Appl. No. 15/074,679.
Final Office Action, dated Jan. 14, 2019, from corresponding U.S. Appl. No. 14/578,039.
Final Office Action, dated Jan. 14, 2019, from corresponding U.S. Appl. No. 15/060,333.
Notice of Allowance, dated Jan. 17, 2019, from corresponding U.S. Appl. No. 14/610,439.
Notice of Allowance, dated Oct. 11, 2018, from corresponding U.S. Appl. No. 15/074,679.
Final Office Action, dated Dec. 11, 2018, from corresponding U.S. Appl. No. 14/610,501.
Office Action, dated Feb. 11, 2019, from corresponding U.S. Appl. No. 14/846,401.
Office Action, dated Apr. 4, 2019, from corresponding U.S. Appl. No. 16/284,615.
Office Action, dated Mar. 21, 2019, from corresponding U.S. Appl. No. 16/259,646.
Final Office Action, dated Apr. 29, 2019, from corresponding U.S. Appl. No. 15/791,196.
Office Action, dated Jun. 11, 2019, from corresponding U.S. Appl. No. 14/610,501.
Office Action, dated Jun. 27, 2019, from corresponding U.S. Appl. No. 15/060,333.
Final Office Action, dated Jul. 18, 2019, from corresponding U.S. Appl. No. 14/846,401.
Office Action, dated Jul. 26, 2019, from corresponding U.S. Appl. No. 16/259,646.
Notice of Allowance, dated Jul. 31, 2019, from corresponding U.S. Appl. No. 16/284,615.
Office Action, dated Aug. 6, 2019, from corresponding U.S. Appl. No. 16/429,480.
Office Action, dated Aug. 7, 2019, from corresponding U.S. Appl. No. 15/611,574.

\* cited by examiner

WEARABLE GAIT MONITORING APPARATUS, SYSTEMS, AND RELATED METHODS

BACKGROUND

Observing a person's gait is often an important clinical step in diagnosing certain types of musculoskeletal and neurological conditions. Proper gait diagnosis may also be valuable in properly fitting a patient with a prosthesis. Currently, gait analysis is largely dependent on the subjective perception of a trained professional. Such manual diagnosis methods may rely on a small set of observable activities and may have inherent inaccuracies, creating the potential for misdiagnosis and the delay of proper treatment. Thus, there is currently a need for improved systems and methods for diagnosing the gait of an individual.

SUMMARY OF VARIOUS EMBODIMENTS

In various embodiments, a method of monitoring the health of an individual comprises: (1) receiving information obtained from at least one sensor worn adjacent the individual's head; (2) in response to receiving the information from a user, utilizing the information to assess the gait of the individual; and (3) at least partially in response to receiving the assessed gait, determining whether the assessed gait includes one or more particular gait patterns that are associated with a particular medical condition.

In various embodiments, a method of monitoring the proper fit of a prosthesis worn by an individual comprises: (1) receiving information obtained from at least one sensor worn adjacent an individual's head; (2) at least partially in response to receiving the information, utilizing the information to assess the gait of the individual and to analyze the assessed gait to determine one or more gait patterns associated with the individual's gait; (3) determining whether the one or more gait patterns are consistent with a particular gait abnormality; and (4) in response to identifying a gait pattern that is consistent with a particular gait abnormality, generating an alert to indicate that the individual may have a gait abnormality, which may further evidence an improper fit of the prosthesis.

In various embodiments, a computer system for monitoring the gait of an individual comprises a pair of glasses comprising one or more sensors for assessing the gait of the individual. In various particular embodiments, the system is configured to analyze a user's assessed gait to determine whether the assessed gait includes one or more particular gait patterns that are consistent with one or more particular medical conditions. In response to determining that the assessed gait includes one or more particular gait patterns that are consistent with one or more particular medical conditions, the system may generate an alert that communicates the particular medical condition to a user (e.g., the individual or a caregiver of the individual).

BRIEF DESCRIPTION OF THE DRAWINGS

Various embodiments of systems and methods for monitoring an individual's gait are described below. In the course of this description, reference will be made to the accompanying drawings, which are not necessarily drawn to scale and wherein.

DETAILED DESCRIPTION OF SOME EMBODIMENTS

Various embodiments will now be described more fully hereinafter with reference to the accompanying drawings. It should be understood that the invention may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Overview

A system, according to various embodiments, includes eyewear (or any other suitable wearable device) that includes one or more sensors (e.g., one or more heart rate monitors, one or more electrocardiograms (EKG), one or more electroencephalograms (EEG), one or more pedometers, one or more thermometers, one or more transdermal sensors, one or more front-facing cameras, one or more eye-facing cameras, one or more microphones, one or more accelerometers, one or more blood pressure sensors, one or more pulse oximeters, one or more respiratory rate sensors, one or more blood alcohol concentration (BAC) sensors, one or more motion sensors, one or more gyroscopes, one or more geomagnetic sensors, one or more global positioning system sensors, one or more impact sensors, or any other suitable one or more sensors) that may be used to monitor the gait of an individual. The system may further include one or more suitable computing devices for analyzing the individual's gait. This information may then be used, for example, to: (1) identify one or more medical conditions associated with the individual; (2) assess the fit of a prosthetic device worn by the individual, and/or (3) assess an individual's recovery from a particular injury or medical procedure.

Exemplary Technical Platforms

As will be appreciated by one skilled in the relevant field, the present invention may be, for example, embodied as a computer system, a method, or a computer program product. Accordingly, various embodiments may take the form of an entirely hardware embodiment, an entirely software embodiment, or an embodiment combining software and hardware aspects. Furthermore, particular embodiments may take the form of a computer program product stored on a computer-readable storage medium having computer-readable instructions (e.g., software) embodied in the storage medium. Various embodiments may take the form of internet-implemented computer software. Any suitable computer-readable storage medium may be utilized including, for example, hard disks, compact disks, DVDs, optical storage devices, and/or magnetic storage devices.

Various embodiments are described below with reference to block diagrams and flowchart illustrations of methods, apparatuses (e.g., systems) and computer program products. It should be understood that each block of the block diagrams and flowchart illustrations, and combinations of blocks in the block diagrams and flowchart illustrations, respectively, can be implemented by a computer executing computer program instructions. These computer program instructions may be loaded onto a general purpose computer, special purpose computer, or other programmable data processing apparatus to produce a machine, such that the instructions which execute on the computer or other programmable data processing apparatus to create means for implementing the functions specified in the flowchart block or blocks.

These computer program instructions may also be stored in a computer-readable memory that can direct a computer or other programmable data processing apparatus to function in a particular manner such that the instructions stored in the computer-readable memory produce an article of manufacture that is configured for implementing the function specified in the flowchart block or blocks. The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the flowchart block or blocks.

Accordingly, blocks of the block diagrams and flowchart illustrations support combinations of mechanisms for performing the specified functions, combinations of steps for performing the specified functions, and program instructions for performing the specified functions. It should also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and other hardware executing appropriate computer instructions.

Example System Architecture

Figure 1:
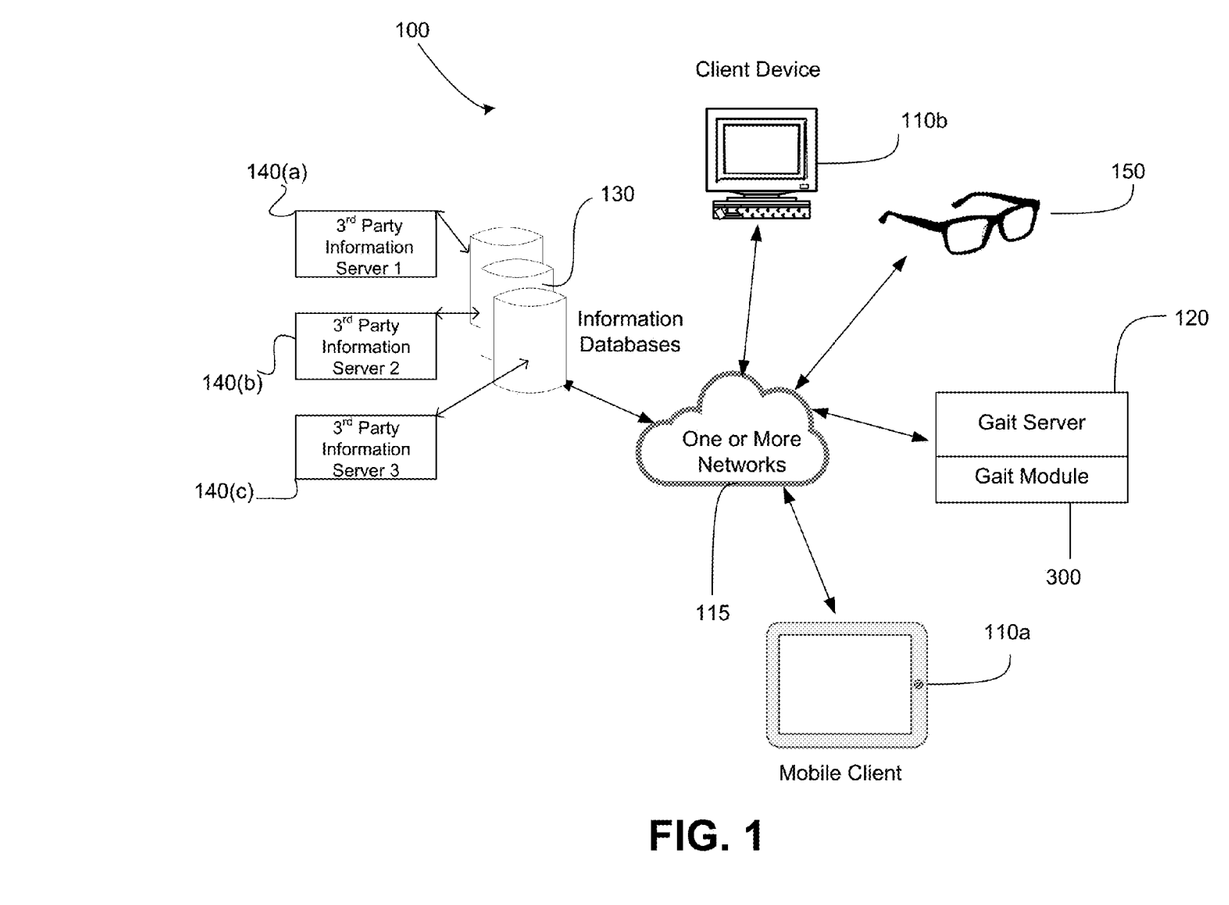
FIG. 1 is a block diagram of an exemplary system for monitoring an individual's gait in accordance with an embodiment of the present system.

FIG. 1 is a block diagram of a Wearable Gait Monitoring System 100 according to a particular embodiment. As may be understood from this figure, the Wearable Gait Monitoring System 100 includes one or more computer networks 115, one or more Third Party Servers 140a, 140b, 140c, a Gait Server 120, a Database 130, one or more remote computing devices 110a, 110b (e.g., such as a smart phone, a tablet computer, a wearable computing device, a laptop computer, etc.), and one or more wearable gait monitoring device(s) 150, which may, for example, be embodied as eyewear (e.g., glasses or goggles), clothing, a watch, a hat, a cast, an adhesive bandage, a piece of jewelry (e.g., a ring, earring, necklace, etc.), and/or any other suitable wearable device.

In various embodiments, the one or more wearable gait monitoring device(s) 150 may further comprise at least one processor and one or more sensors (e.g., an accelerometer, a magnetometer, a gyroscope, a front-facing camera, a location sensor such as a GPS unit, etc.). In particular embodiments, the system is configured to gather data, for example, using the one or more sensors, regarding the user's gait as the user walks or runs (e.g., the user's stride cadence, the user's speed (e.g., the speed of the user's feet and/or body), the orientation of the user (e.g., the orientation of the user's body and/or feet), the elevation of the user's respective feet from the ground, the movement of the user's head such as bobbing, etc.).

In various embodiments, the database is configured to store information regarding gait patterns associated with various predetermined medical conditions. The system is configured to store information regarding normal gait patterns for a particular individual or individuals who are similar in physical stature to the particular individual. In various embodiments, the database stores past information regarding an individual's gait and may include recent gait measurements for the individual, which may, for example, be used to track the individual's progress in improving their gait (e.g., after an injury or a medical procedure).

The one or more computer networks 115 may include any of a variety of types of wired or wireless computer networks such as the Internet, a private intranet, a mesh network, a public switch telephone network (PSTN), or any other type of network (e.g., a network that uses Bluetooth or near field communications to facilitate communication between computers). The communication link between the Wearable Gait Monitoring System 100 and the Database 130 may be, for example, implemented via a Local Area Network (LAN) or via the Internet. In particular embodiments, the one or more computer networks 115 facilitate communication between the one or more third party servers 140a, 140b, 140c, the Gait Server 120, the Database 130, and one or more remote computing devices 110a, 110b. In various embodiments, the handheld device 110a is configured to communicate with the wearable gait monitoring device 150 via, for example, Bluetooth. In various other embodiments, the wearable gait monitoring device 150 may communicate with a remote server, for example, the Gait Server 120, via a cellular communication or wireless Internet connection. In yet other embodiments, the system may be further configured to allow the wearable gait monitoring device 150 to communicate with the remote server (e.g., the Gait Server 120), without the intermediary handheld device 110a.

Figure 2:
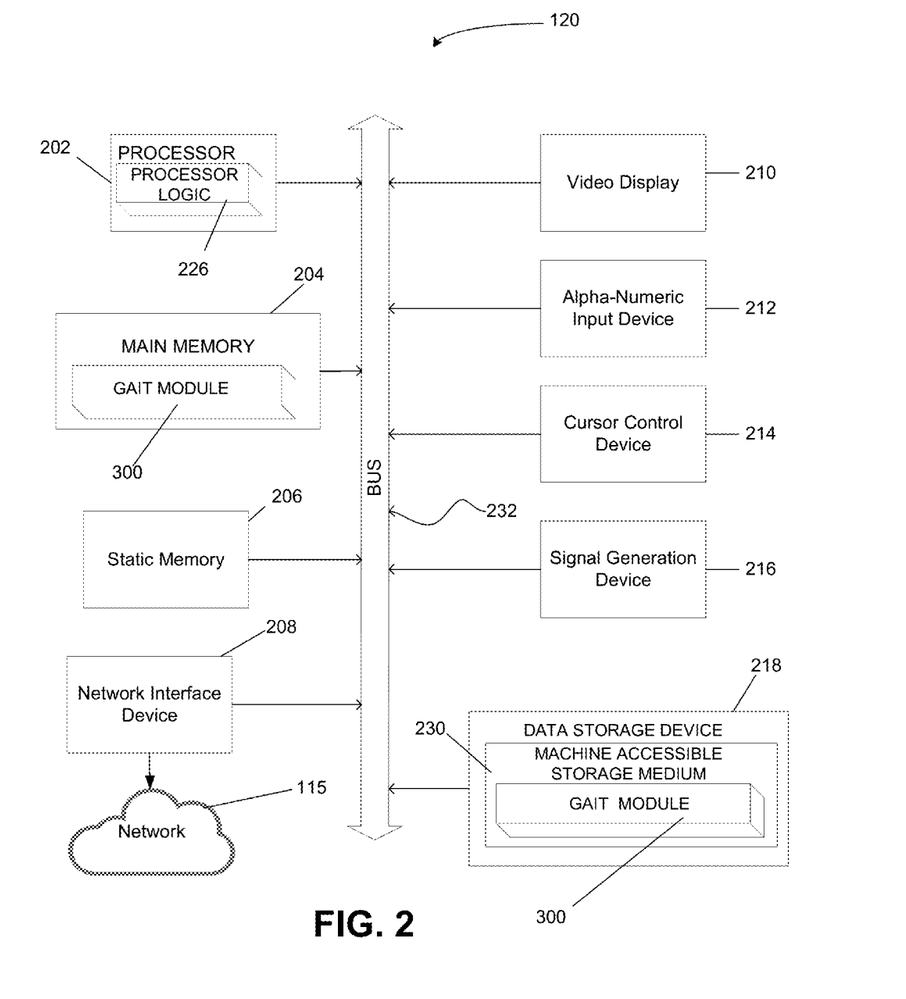
FIG. 2 is a block diagram of a gait analysis server that may be used in the system shown in FIG. 1.

FIG. 2 illustrates a diagrammatic representation of a computer architecture that can be used within the Wearable Gait Monitoring System 100, for example, as a client computer (e.g., one of computing devices 110a/110b or wearable gait monitoring devices 150), or as a server computer (e.g., the Gait Server 120) as shown in FIG. 1. In particular embodiments, the Gait Server 120 may be suitable for use as a computer, within the context of the wearable gait monitoring system 100, that is configured to record medical information for use in gait analysis and to provide communication between one or more users and healthcare practitioners.

In particular embodiments, the Gait Server 120 may be connected (e.g., networked) to other computers in a LAN, an intranet, an extranet, and/or the Internet. As noted above, the Gait Server 120 may operate in the capacity of a server or a client computer in a client-server network environment, or as a peer computer in a peer-to-peer (or distributed) network environment. The Gait Server 120 may be a desktop personal computer (PC), a tablet PC, a set-top box (STB), a Personal Digital Assistant (PDA), a cellular telephone, a web appliance, a server, a network router, a switch or bridge, or any other computer capable of executing a set of instructions (sequential or otherwise) that specify actions to be taken by that computer. Further, while only a single computer is illustrated, the term "computer" shall also be taken to include any collection of computers that individually or jointly execute a set (or multiple sets) of instructions to perform any one or more of the methodologies discussed herein.

An exemplary Gait Server 120 includes a processing device 202, a main memory 204 (e.g., read-only memory (ROM), flash memory, dynamic random access memory (DRAM) such as synchronous DRAM (SDRAM) or Rambus DRAM (RDRAM), etc.), a static memory 206 (e.g., flash memory, static random access memory (SRAM), etc.), and a data storage device 218, which communicate with each other via a bus 232.

The processing device 202 represents one or more general-purpose processing devices such as a microprocessor, a central processing unit, or the like. More particularly, the processing device 202 may be a complex instruction set computing (CISC) microprocessor, reduced instruction set computing (RISC) microprocessor, very long instruction word (VLIW) microprocessor, or processor implementing other instruction sets, or processors implementing a combination of instruction sets. The processing device 202 may also be one or more special-purpose processing devices such as an application specific integrated circuit (ASIC), a field programmable gait array (FPGA), a digital signal processor (DSP), network processor, or the like. The processing device 202 may be configured to execute processing logic 226 for performing various operations and steps discussed herein.

The Gait Server 120 may further include a network interface device 208. The Gait Server 120 also may include a video display unit 210 (e.g., a liquid crystal display (LCD) or a cathode ray tube (CRT)), an alphanumeric input device 212 (e.g., a keyboard), a cursor control device 214 (e.g., a mouse), and a signal generation device 216 (e.g., a speaker).

The data storage device 218 may include a non-transitory computer-accessible storage medium 230 (also known as a non-transitory computer-readable storage medium or a non-transitory computer-readable medium) on which is stored one or more sets of instructions (e.g., software 222) embodying any one or more of the methodologies or functions described herein. The software 222 may also reside, completely or at least partially, within the main memory 204 and/or within the processing device 202 during execution thereof by the Gait Server 120—the main memory 204 and the processing device 202 also constituting computer-accessible storage media. The software 222 may further be transmitted or received over a network 115 via a network interface device 208.

While the computer-accessible storage medium 230 is shown in an exemplary embodiment to be a single medium, the terms "computer-accessible storage medium" and "computer-readable medium" should be understood to include a single medium or multiple media (e.g., a centralized or distributed database, and/or associated caches and servers) that store the one or more sets of instructions. The term "computer-accessible storage medium" and "computer-readable medium" should also be understood to include any medium that is capable of storing, encoding or carrying a set of instructions for execution by the computer and that cause the computer to perform any one or more of the methodologies of the present invention. The terms "computer-accessible storage medium" and "computer-readable medium" should accordingly be understood to include, but not be limited to, solid-state memories, optical and magnetic media, etc.

More Detailed Description of Gait Monitoring Functionality

Various embodiments of a system for the monitoring the gait of an individual are described below and may be implemented in any suitable context. For example, particular embodiments may be implemented to: (1) identify one or more medical conditions associated with the individual; (2) assess the fit of a prosthetic device worn by the individual, and/or (3) assess an individual's recovery from a particular injury or medical procedure.

Figure 3:
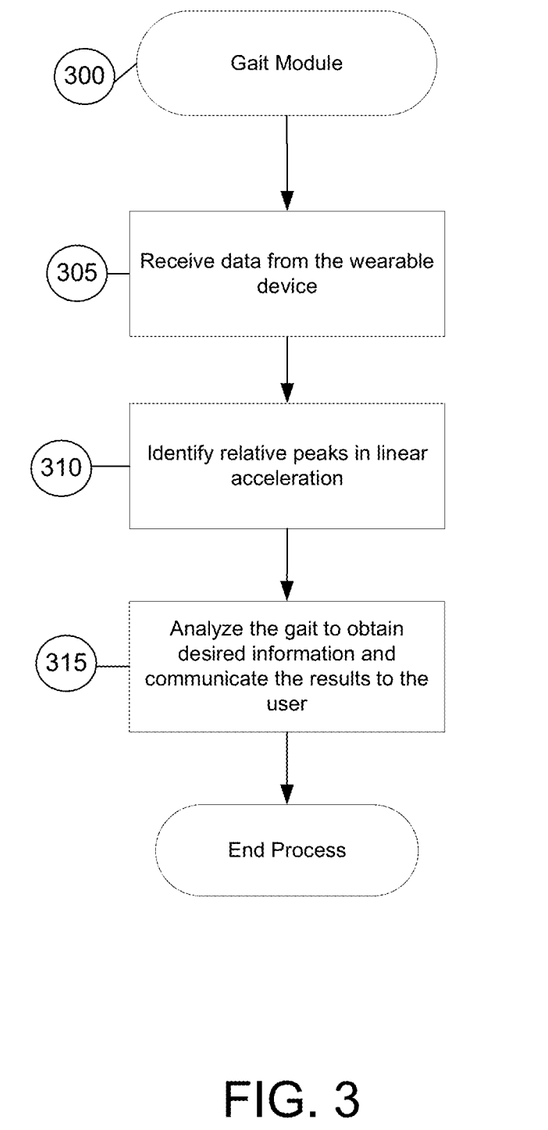
FIG. 3 depicts a flowchart that generally illustrates a method of monitoring an individual's gait.

Various aspects of the system's functionality may be executed by certain system modules, including the Gait Monitoring Module 300. The Gait Monitoring Module 300 is discussed in greater detail below.

Gait Monitoring Module

Referring to FIG. 3A, when executing the Gait Monitoring Module 300, the system begins, in various embodiments, at Step 305 by receiving data from a wearable device worn by an individual whose gait is to be monitored by the system. In particular embodiments, the system is configured to receive data from one or more sensors (e.g. an accelerometer, a gyroscope, a position locating device and/or magnetometer) while: (1) the individual is wearing the wearable device adjacent the user's face and/or head; and (2) the individual is walking or running. In particular embodiments, the system is configured to receive the data while the individual is walking or running within the context of their typical daily routine, and not within the context of a medical diagnostic visit. The system may also or alternatively be configured to receive data within the context of a medical diagnostic visit (e.g., at a doctor's office, hospital, or other medical facility).

In particular embodiments, the one or more of the system's sensors may be embedded in, or otherwise attached to, eyewear or other wearable device (e.g., another wearable device worn adjacent the individual's head or another suitable part of the individual's body). In particular embodiments, at least one or more of the system's sensors may be incorporated into a prosthesis or into a portion of the individual's shoes. In certain embodiments, the system may include one or more sensors that are incorporated into (e.g., embedded in, or attached to) a plurality of wearable devices (e.g., eyewear and the individual's shoes) that are adapted to be worn simultaneously by the user while the system retrieves signals from the sensors to assess the individual's gait.

In particular embodiments, the system may include a set of eyewear that includes one or more motion sensors (e.g., accelerometers, gyroscopes, or location sensors) for sensing the movement of the head of an individual who is wearing the eyewear as the individual walks. The system may then use this head movement information (e.g., using any suitable technique, such as any suitable technique described herein) to determine whether the user has a gait abnormality. The system may do this, for example, by comparing one or more of the measured head motions of an individual (e.g., as measured when the individual is walking or running) with the actual or typical head motions experienced by individuals with gait abnormalities as those individuals walk or run.

In various embodiments, the system is configured to measure and receive at least one of the velocity, height, and orientation of one or more of the individual's feet. For example, in certain embodiments, the system is configured to measure and receive (e.g., using the suitable sensors) the linear acceleration of each of the individual's feet, the height of each of the feet from the ground, and/or the position and/or orientation of each of the feet relative to the central axis of the individual's body as the individual walks or runs.

The system continues at Step 310 by using the data received from the system's sensors to identify one or more relative peaks in linear acceleration of the individual's body and/or head as the user ambulates (e.g., walks or runs). In various embodiments, the system may do this by processing the data received from the sensor(s) in Step 305, and then isolating the relative peaks in the data. Such peaks represent the relative maxima and minima of the linear acceleration of the user's head, body, and/or one or more of the individual's lower body parts (e.g., knee, ankle, or foot) as the user ambulates. Alternatively or additionally, the system may be configured to identify the relative peaks in linear acceleration by identifying the slope of the line formed by regression analysis of the data received from the sensors. This regression analysis may indicate the change in magnitude of the linear acceleration with time.

In identifying the relative peaks in linear acceleration, the system is further configured to identify the peaks such that the magnitude and phase of these peaks may be utilized to aid in the diagnosis of one or more gait abnormalities by comparing the magnitude and phase of the peaks associated with the individual's gait with the magnitude and phase of the peaks associated with: (1) the gait of one or more individuals who are known to have one or more gait abnormalities; (2) a typical gait associated with individuals who are known to have one or more gait abnormalities; and/or (3) the individual's normal gait (which may be determined based on data stored in system memory that the system obtained, for example, when the individual was known to walk or run without a gait abnormality). This comparison may be helpful in determining whether the individual has a gait abnormality and, if so, whether the gait abnormality exists due to an improper prosthetic fit.

In a particular embodiment, the above comparison may involve comparing the magnitude and/or phase of peaks that represent a user's head movement as the user ambulates with the magnitude and/or phase of peaks that represent the head movement, during ambulation, of (1) one or more individuals who are known to have one or more gait abnormalities; (2) a typical individual (or model theoretical individual) who is known to have one or more gait abnormalities; and/or (3) the individual themself (this data may be determined, for example, based on data stored in system memory that the system obtained, for example, when the individual was known to walk or run without a gait abnormality).

Continuing at Step 315, the system is configured to analyze the received gait information to determine whether the individual has an identifiable gait abnormality and to communicate the results of the analysis to the user. In various embodiments, the system may use the gait information to: (1) identify potential, previously undiagnosed medical conditions (e.g., one or more medical conditions, such as ALS or MS, that may be indicated by a particular gait abnormality, such as foot drop); (2) assess the quality of the fit of a prosthesis; and/or (3) assess the individual's progress in recovering from an injury or medical procedure (e.g., knee or hip surgery).

Use of System to Identify Previously Undiagnosed Medical Condition

In identifying a potential, previously undiagnosed medical condition, the system is configured to compare the gait of the individual with: (1) the gait of one or more individuals who are known to have one or more gait abnormalities (e.g., hemiplegic gait, diplegic gait, neuropathic gait, foot drop, myopathic gait, or ataxic gait); (2) a typical gait associated with individuals who are known to have one or more gait abnormalities; and/or (3) the individual's normal gait. To do this, the system may compare one or more gait patterns of a user (e.g., in the manner discussed above or in any other suitable way) with information regarding one or more abnormal gait patterns that is stored in a Gait Database 130. The system may do this, for example, by applying any suitable mathematical or other data comparison technique to determine whether one of more of the individual's gait patterns are at least substantially similar to one or more abnormal gait patterns stored in the system's Gait Database 130.

If the system determines that the individual has, or may have, a particular gait abnormality, the system may generate and send a notification to a suitable individual (e.g., the individual or the individual's physician) indicating that the individual may have a gait abnormality and/or that it may be beneficial to examine or monitor the individual for one or more medical conditions that are typically associated with the gait abnormality, e.g., stroke, amyotrophic lateral sclerosis, muscular dystrophy, Charcot Maries Tooth disease, multiple sclerosis, cerebral palsy, hereditary spastic paraplegia, and Friedrich's ataxia. The notification may be, for example, a suitable electronic notification (e.g., a message on a display screen, an e-mail, a text), or any other suitable notification.

Use of System to Determine Whether a Prosthesis Fits Correctly

In assessing the quality of fit of the prosthesis, the system in various embodiments, may, in various embodiments, be configured to compare the user's assessed gait with: (1) the gait of one or more individuals who are known to have one or more gait abnormalities that are associated with an improper prosthetic fit; (2) a typical gait associated with individuals who are known to have one or more gait abnormalities that are associated with an improper prosthetic fit; and/or (3) the individual's normal gait. This comparison may be done as discussed above or in any other suitable way. In particular embodiments, the gait patterns that the individual's gait patterns are compared with may be modeled, for example, based on previously recorded data for individuals with one or more physical attributes (e.g., height, age, weight, femur length, etc . . . ) that are similar to that of the individual. In various other embodiments, such patterns may be modeled from previously recorded data for users that aren't physically similar to the individual.

In response to determining that the individual has one or more gait patterns that are associated with an improper prosthetic fit, the system may generate an alert indicating that the prosthesis may fit improperly. The system may send this alert electronically, for example, via email, text message, or via a display on a display screen, to the user and/or their physician or other suitable individual.

In various embodiments, after determining that the individual has an abnormal gait, the system may then determine whether the gait deviation results from an improperly fitting prosthesis or from an injury associated with the individual (e.g., an infected wound adjacent the prosthesis). It is noted that an improper fit of a prosthetic leg may result in any of a number of gait deviations such as trans-femoral (TF) long prosthetic step, TF excessive lumbar lordosis, TF drop off at end of stance, TF foot slap, TF medial or lateral whips, TF uneven heel rise, etc. While such gait deviations may result from an improper prosthetic fit, they may also manifest from: (1) various improper actions or movements by the amputee while the amputee is wearing the prosthesis; or (2) an injury adjacent the prosthesis. Clinically distinguishing an improper gait caused by a poorly fitting prosthetic from an improper gait caused by improper use of a properly fitted prosthesis may be important in helping the amputee regain proper functionality of the prosthetic.

Use of System to Assess an Individual's Recovery from an Injury or Medical Procedure In assessing an individual's recovery from an injury or medical procedure, the system may compare the individual's current gait with historical gait information for the individual stored in the Database 130. The historical gait information, in various embodiments, may include gait pattern information taken for the individual at some time in the past (e.g., the recent past) before or after the user suffered the injury or underwent the medical procedure.

The system may then analyze both sets of gait information to determine whether the individual's gait has become more consistent with the user's normal gait (e.g., fewer abnormalities in gait, more regular, quicker lateral acceleration, etc.) To do this, the system may, in various embodiments, compare the user's current gait information with a normal gait to determine whether the user's gait has become more consistent with a normal gait over time. In other embodiments, the system may compare the most current gait data with other post-procedure or post-injury gait data for the individual to determine whether the user's gait has become more consistent with a normal gait (e.g., the individual's normal gait).

Upon analyzing both sets of gait information, the system may generate an appropriate assessment of the user's recovery and/or to generate one or more treatment recommendations. The system may, in various embodiments, generate a report that communicates the progress of an individual's recovery. The system may also, or alternatively, generate an alternate treatment plan for the individual, if necessary. For example, a particular generated report may include one or more recommendations with regard to a particular type and length of physical therapy to be performed by the individual, and/or one or more dietary restrictions that the individual should implement to aid recovery to regain muscle tone and strength in the affected limb. The system may then communicate the report to the individual or an appropriate third party.

User Experience

Gait Abnormality Diagnosis

In a particular example, a pair of eyewear with embedded sensors may be used to monitor the user's gait over the course of one or more days (e.g., days, weeks, months, years, etc.). As the sensors measure the movements of the individual's body (e.g., the individual's head, legs, feet, etc . . . ), the system may transmit the related movement data to a remote server where the information is stored in a suitable database. After receiving the data, a central server may process the data to identify one or more gait patterns for the individual. The system may then compare one or more of the individual's gait patterns with one or more known irregular gait patterns to determine whether the individual has an irregular gait pattern as discussed above.

The system may be utilized, for example, in the following construct. A patient may present to a physician complaining of weakness and decreased use of one leg. The physician may perform a routine physical, ask diagnostic questions, and have the patient walk briefly in order to physically demonstrate the purported condition. Upon observing the patient, the doctor may decide that the patient may potentially have a gait abnormality, but the physician cannot isolate the specific abnormality as presented by the patient. The physician may instruct the patient to wear the wearable gait monitoring device over the course of one or more days. During this time, the wearable gait monitoring device would obtain and record information regarding the individual's gait as discussed above.

The system may then use the information to identify one or more gait pattern irregularities as discussed above and generate a message to the user's treating physician indicating that the individual appears to have an abnormal gait. The system may optionally further display one or more potential medical conditions associated with that gait, e.g., amyotrophic lateral sclerosis, multiple sclerosis, etc. The physician may then meet with the individual to discuss the individual's condition, and/or to order additional testing to establish a particular diagnosis. For example, the physician may review the patient's medical history, presented gait pattern, and possible conditions contributing to the gait abnormality to diagnose and/or to order more tests to aid in the diagnosis of such medical conditions.

The system may similarly be used to analyze the fit of a particular prosthetic, or a user's recovery from an injury or surgery using similar techniques in combination with one or more of the methods described above.

CONCLUSION

Many modifications and other embodiments of the invention will come to mind to one skilled in the art to which this invention pertains, having the benefit of the teaching presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for the purposes of limitation.

We claim:

1. A non-transitory computer-readable medium storing computer-executable instructions for:

receiving, at a gait server, a first set of information obtained over a first period of time defined by an individual's routine movements from at least one sensor embedded into a pair of glasses worn by the individual and from at least one sensor positioned proximate at least one foot of the individual, wherein the first set of information corresponds to one or more movements of the individual's head, to a height of the at least one foot from the ground, and to an orientation of the at least one foot relative to a central axis of the individual as the individual ambulates;

using, by the gait server, the first set of information to identify one or more relative peaks in linear acceleration of the head of the individual;

using, by the gait server, regression analysis techniques to identify a first slope of a first line corresponding to the one or more relative peaks in linear acceleration of the head of the individual over the first period of time to identify a first gait pattern of the individual;

receiving, at the gait server, a second set of information obtained over a second period of time defined by the individual's routine movements from the at least one sensor embedded into the pair of glasses worn by the individual and from the at least one sensor positioned proximate to the at least one foot of the individual, wherein the second set of information corresponds to one or more movements of the individual's head, to the height of the at least one foot from the ground, and to the orientation of the at least one foot relative to the central axis of the individual as the individual ambulates;

using, by the gait server, the second set of information to identify one or more relative peaks in linear acceleration of the head of the individual;

using, by the gait server, regression analysis techniques to identify a second slope of a second line corresponding to the one or more relative peaks in linear acceleration of the head of the individual over the second period of time to identify a second gait pattern of the individual;

comparing, by the gait server, the first gait pattern to the second gait pattern by comparing the first slope of the first line to the second slope of the second line;

in response to comparing the first gait pattern to the second gait pattern, identifying, by the gait server, the second gait pattern as an irregular gait pattern;

analyzing, by the gait server, the irregular gait pattern to determine whether the irregular gait pattern includes one or more particular gait patterns that are associated with a particular medical condition; and in response to determining that the irregular gait pattern includes the one or more gait patterns, generating an alert that the individual may have the particular medical condition.

2. The non-transitory computer-readable medium of claim 1, wherein the at least one sensor is a gyroscope.

3. The non-transitory computer-readable medium of claim 1, wherein the step of analyzing the irregular gait pattern to determine whether the irregular gait pattern includes one or more particular gait patterns that are associated with a particular medical condition comprises:

comparing the one or more movements of the individual's head, the height of the at least one foot from the ground, and the orientation of the at least one foot with one or more head movements, foot movements, and foot orientations that are associated with the particular medical condition; and at least partially in response to determining that the one or more movements of the individual's head, the height of the at least one foot from the ground, or the orientation of the at least one foot correspond to one or more head movements, foot heights, or foot orientations that are associated with the particular medical condition, determining that the irregular gait pattern includes one or more particular gait patterns that are associated with the particular medical condition.

4. The non-transitory computer-readable medium of claim 1, wherein the one or more gait patterns is foot drop.

5. The non-transitory computer-readable medium of claim 4, wherein the particular medical condition is a medical condition selected from a group consisting of: stroke, amyotrophic lateral sclerosis, muscular dystrophy, Charcot Marie Tooth disease, multiple sclerosis, cerebral palsy, hereditary spastic paraplegia, and Friedrich's ataxia.

6. The non-transitory computer-readable medium of claim 1, wherein the one or more gait patterns is propulsive gait.

7. The non-transitory computer-readable medium of claim 6, wherein the particular medical condition is a medical condition selected from a group consisting of: carbon monoxide poisoning, manganese poisoning, and Parkinson's disease.

8. The non-transitory computer-readable medium of claim 1, wherein the one or more gait patterns is waddling gait.

9. The non-transitory computer-readable medium of claim 8, wherein the particular medical condition is a medical condition selected from a group consisting of: congenital hip dysplasia, muscular dystrophy, and spinal muscle atrophy.

10. The non-transitory computer-readable medium of claim 1, wherein the step of analyzing the irregular gait pattern to determine whether the irregular gait pattern includes one or more particular gait patterns that are associated with a particular medical condition comprises:

comparing the irregular gait pattern with the one or more gait patterns that are associated with the particular medical condition; and in response to determining that the irregular gait pattern corresponds to the one or more gait patterns that are associated with the particular medical condition, determining that the irregular gait pattern includes one or more particular gait patterns that are associated with a particular medical condition.

11. The non-transitory computer-readable medium of claim 10, wherein the step of comparing the irregular gait pattern with the one or more gait patterns that are associated with the particular medical condition comprises comparing one or more relative peaks in linear acceleration associated with the irregular gait pattern of the individual with one or more relative peaks in linear acceleration of the one or more gait patterns that are associated with the particular medical condition.

12. A system for monitoring the gait of an individual, said system comprising:

a pair of glasses comprising one or more sensors for assessing the gait of the individual during a period of time corresponding to a recovery;

a computer system comprising a processor in communication with the one or more sensors of the pair of glasses, the processor being configured to:

obtain a first set of information over a first time after an injury or a medical procedure from the one or more sensors of the pair of glasses worn by the individual;

assess a first injury gait associated with the individual's gait during the first time, wherein assessing the first injury gait comprises:

using the first set of information to identify one or more relative peaks in linear acceleration of a head of the individual, and using regression analysis techniques to identify a first slope of a first line corresponding to the one or more relative peaks in linear acceleration of the head of the individual over the first period of time to identify the first injury gait pattern of the individual;

obtain a second set of information over a second time after the injury or the medical procedure from the one or more sensors of the pair of glasses worn by the individual;

assess a second injury gait associated with the individual's gait during the second time, wherein the first time is closer to the injury or the medical procedure than the second time, wherein assessing the second injury gait comprises:

using the second set of information to identify one or more relative peaks in linear acceleration of the head of the individual, and using regression analysis techniques to identify a second slope of a second line corresponding to the one or more relative peaks in linear acceleration of the head of the individual over the second period of time to identify the second injury gait pattern of the individual;

analyze the first injury gait and the second injury gait to determine whether the individual's gait is normalizing to become more consistent with a previously established one or more movement patterns associated with the individual prior to the injury or the medical procedure;

in response to determining that the individual's gait is not becoming more consistent with a previously established one or more movement patterns associated with the individual prior to the injury or the medical procedure, determine an alternate treatment plan for the individual; and generate an alert to the individual comprising the alternate treatment plan.

13. A non-transitory computer-readable medium storing computer-executable instructions for:
- receiving, at a gait server, a first set of information obtained over a first period of time defined by an individual's routine movements from at least one sensor embedded into a pair of glasses worn by the individual, wherein the first set of information corresponds to one or more movements of the individual's head as the individual ambulates;
- using, by the gait server, the first set of information to identify one or more relative peaks in linear acceleration of the head of the individual;
- using, by the gait server, regression analysis techniques to identify a first slope of a first line corresponding to the one or more relative peaks in linear acceleration of the head of the individual over the first period of time to identify a first gait pattern of the individual;
- receiving, at the gait server, a second set of information obtained over a second period of time defined by the individual's routine movements from the at least one sensor embedded into the pair of glasses worn by the individual, wherein the second set of information corresponds to one or more movements of the individual's head as the individual ambulates;
- using, by the gait server, the second set of information to identify one or more relative peaks in linear acceleration of the head of the individual;
- using, by the gait server, regression analysis techniques to identify a second slope of a second line corresponding to the one or more relative peaks in linear acceleration of the head of the individual over the second period of time to identify a second gait pattern of the individual;
- comparing, by the gait server, the first gait pattern to the second gait pattern by comparing the first slope of the first line to the second slope of the second line;
- in response to comparing the first gait pattern to the second gait pattern, identifying, by the gait server, the second gait pattern as an irregular gait pattern;
- analyzing, by the gait server, the irregular gait pattern to determine whether the irregular gait pattern includes one or more particular gait patterns that are associated with a particular medical condition; and
- in response to determining that the irregular gait pattern includes the one or more gait patterns, generating an alert that the individual may have the particular medical condition.

* * * * *